(12) United States Patent
Potter et al.

(10) Patent No.: US 7,727,223 B2
(45) Date of Patent: Jun. 1, 2010

(54) DRUG DELIVERY TECHNOLOGY

(75) Inventors: Charles David Ogilvy Potter, Oxfordshire (GB); David Stuart Potter, Isle of White (GB)

(73) Assignee: Glide Pharmaceutical Technologies Limited, Oxfordshire (GB)

( * ) Notice: Subject to any disclaimer, the term of this patent is extended or adjusted under 35 U.S.C. 154(b) by 590 days.

(21) Appl. No.: 10/489,265

(22) PCT Filed: Sep. 10, 2002

(86) PCT No.: PCT/EP02/10394

§ 371 (c)(1),
(2), (4) Date: Sep. 7, 2004

(87) PCT Pub. No.: WO03/023773

PCT Pub. Date: Mar. 20, 2003

(65) Prior Publication Data

US 2005/0013840 A1    Jan. 20, 2005

(30) Foreign Application Priority Data

Sep. 11, 2001  (GB) ................................ 0121914.6

(51) Int. Cl.
*A61M 31/00*    (2006.01)
*A61K 9/14*    (2006.01)
(52) U.S. Cl. ........................... 604/506; 604/57; 424/486
(58) Field of Classification Search ................. 424/422, 424/426, 423; 604/68–72; 102/502
See application file for complete search history.

(56) References Cited

U.S. PATENT DOCUMENTS 1,819,415 A  *  8/1931  Harris ......................... 102/512

| | | | |
|---|---|---|---|
| 2,398,544 A | | 4/1946 | Lockhart |
| 2,752,918 A | | 7/1956 | Uytenbogaart |
| 3,616,758 A | * | 11/1971 | Komarov ..................... 102/512 |
| 3,901,158 A | | 8/1975 | Ferb |

(Continued)

FOREIGN PATENT DOCUMENTS

CA        1019638        10/1977

(Continued)

OTHER PUBLICATIONS

European Patent Office, Search and Examination Report, Application GB0605772.3, Apr. 26, 2006.

(Continued)

*Primary Examiner*—Tatyana Zalukaeva
*Assistant Examiner*—Michael J Anderson
(74) *Attorney, Agent, or Firm*—Robert L. Kelly; Dickinson Wright

(57) ABSTRACT

The invention relates to a novel drug delivery technology. More particularly the invention relates to a method of delivering at least one therapeutic compound or a formulation comprising the at least one therapeutic compound to a patient: to a throwaway or reusable device for delivering at least one therapeutic compound or a formulation comprising the at least one therapeutic compound to a patient in a manner as set out by the method; to a pioneer projectile form use in said method; to formulations for use in said method and to an injectate comprising a pioneer projectile and formulation. It also relates to a disposable component containing either a pioneer projectile or an injectate.

5 Claims, 7 Drawing Sheets

U.S. PATENT DOCUMENTS

| | | | |
|---|---|---|---|
| 3,948,263 A | | 4/1976 | Drake, Jr. et al. |
| 3,982,536 A | * | 9/1976 | Krogseng et al. ............ 424/422 |
| 4,059,107 A | | 11/1977 | Iriguchi et al. |
| 4,116,196 A | | 9/1978 | Kaplan et al. |
| 4,326,524 A | | 4/1982 | Drake, Jr. et al. |
| 4,419,936 A | * | 12/1983 | Coates et al. ................ 102/364 |
| 4,449,982 A | | 5/1984 | Gould, III .................... 424/422 |
| 4,518,387 A | | 5/1985 | Murphy et al. |
| 4,664,664 A | * | 5/1987 | Drake, Jr. .................... 102/502 |
| 4,790,824 A | | 12/1988 | Morrow et al. |
| 4,808,184 A | | 2/1989 | Tepic |
| 4,863,429 A | | 9/1989 | Baldwin |
| 4,871,094 A | | 10/1989 | Gall et al. |
| 4,968,302 A | | 11/1990 | Schluter et al. |
| 5,092,842 A | | 3/1992 | Bechtold et al. |
| 5,116,313 A | | 5/1992 | Gregor |
| 5,206,024 A | * | 4/1993 | Peery et al. .................. 424/438 |
| 5,354,287 A | * | 10/1994 | Wacks ......................... 604/232 |
| 5,360,410 A | | 11/1994 | Wacks |
| 5,542,920 A | | 8/1996 | Cheikh |
| 5,549,560 A | | 8/1996 | Van de Wijdeven |
| 5,589,167 A | * | 12/1996 | Cleland et al. .............. 424/85.7 |
| 5,599,302 A | | 2/1997 | Lilley et al. |
| 5,747,058 A | * | 5/1998 | Tipton et al. ................. 424/423 |
| 6,001,385 A | * | 12/1999 | Van De Wijdeven ........ 424/422 |
| 6,102,896 A | | 8/2000 | Roser |
| 6,117,443 A | | 9/2000 | Cheikh |
| 6,120,786 A | | 9/2000 | Cheikh |
| 6,203,521 B1 | | 3/2001 | Menne et al. |
| 6,264,629 B1 | * | 7/2001 | Landau ......................... 604/68 |
| 6,331,310 B1 | | 12/2001 | Roser et al. |
| 6,375,971 B1 | * | 4/2002 | Hansen ........................ 424/422 |
| 6,586,006 B2 | * | 7/2003 | Roser et al. ................. 424/484 |
| 6,689,093 B2 | | 2/2004 | Landau |
| 6,783,509 B1 | | 8/2004 | Landau et al. |

FOREIGN PATENT DOCUMENTS

| | | |
|---|---|---|
| DE | 3644984 A1 | 7/1988 |
| DE | 3839287 | 5/1990 |
| EP | 0 008 636 | 6/1982 |
| EP | 0139286 | 5/1985 |
| EP | 0 119 286 B1 | 12/1987 |
| EP | 0 276 158 A2 | 7/1988 |
| EP | 0 276 158 A3 | 7/1988 |
| EP | 0 427 457 A2 | 5/1991 |
| EP | 0 427 457 B1 | 5/1991 |
| EP | 0 518 561 A1 | 12/1992 |
| EP | 0 409 365 B1 | 4/1994 |
| EP | 0 595 508 B1 | 5/1994 |
| EP | 0 666 084 A2 | 8/1995 |
| EP | 0 666 084 B1 | 8/1995 |
| EP | 0 879 609 A2 | 11/1998 |
| EP | 0 879 609 B1 | 7/2002 |
| FR | 1014881 | 6/1952 |
| FR | 1049564 | 12/1953 |
| FR | 2 627 698 | 3/1988 |
| FR | 2749764 | 6/1996 |
| GB | 993309 | 5/1965 |
| GB | 2 193 644 A | 2/1988 |
| GB | 2 239 180 A | 6/1991 |
| GB | 2 365 100 A | 2/2002 |
| GB | 2365100 | 2/2002 |
| WO | WO 94/07553 | 4/1994 |
| WO | WO 9422423 | 10/1994 |
| WO | WO-96/40351 | 12/1996 |
| WO | WO 00/62734 | 10/2000 |
| WO | WO 02/48654 A1 | 12/2001 |

OTHER PUBLICATIONS

International Search Report, Application No. PCT/EP 02/10394.
Search Report, Application No. GB 0121914.6, dated Jun. 7, 2002.
Search Report, Application No. GB 0121914.6, dated Aug. 8, 2002.
Co-Pending U.S. Appl. No. 10/523,473.
Co-Pending U.S. Appl. No. 10/238,415.

* cited by examiner

FIG 5b 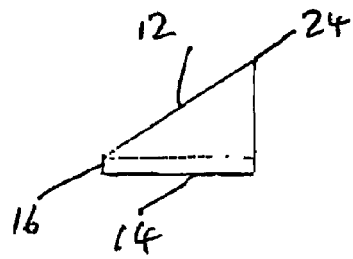  FIG 5c

FIG 6b 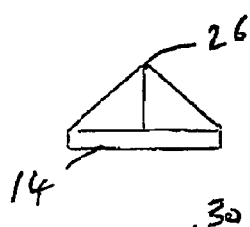 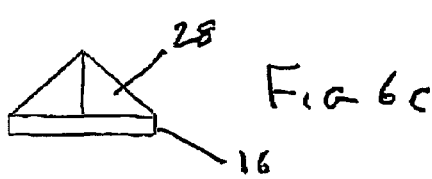 FIG 6c

FIG 7b 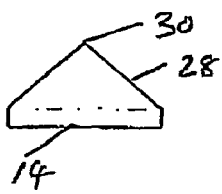 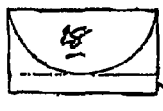 FIG 7c

FIG 8b 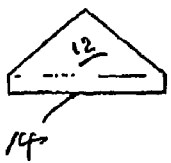 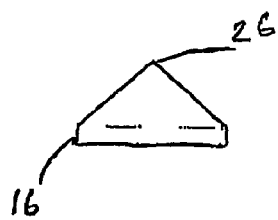 FIG 8c

DRUG DELIVERY TECHNOLOGY

FIELD OF THE INVENTION

The present invention relates to a novel drug delivery technology. More particularly the invention relates to a method of delivering at least one therapeutic compound or a formulation comprising the at least one therapeutic compound to a patient; to a throwaway or reusable device for delivering at least one therapeutic compound or a formulation comprising the at least one therapeutic compound to a patient in a manner as set out by the method; to a pioneer projectile for use in said method; to formulations for use in said method and to an injectate comprising a pioneer projectile and formulation. It also relates to a disposable component containing either a pioneer projectile or an injectate.

BACKGROUND TO THE INVENTION

One route of administration for therapeutic compounds is through the skin. The skin is also one of the more efficient routes for delivery of a therapeutic compound when compared to other standard delivery routes such as oral or pulmonary delivery.

Administration to the skin is most commonly undertaken using a needle and syringe as a delivery system with the therapeutic compound in a liquid form.

Such a system has a number of associated problems including the pain and fear associated with needles, the fact they are really best suited to injecting liquids which are not necessarily the best way of delivering compounds to a patient and the fact that sharps are left which create a disposal problem.

Drug delivery systems that do not incorporate needles are also used for injecting liquids through the skin and this is achieved by the delivery system creating a very fine, high velocity liquid jet that creates its own hole through the skin. There are however a number of problems with such a method including splash back.

With both these forms of liquid delivery relatively large volumes of liquid are injected which, because they are incompressible, have to tear the tissue apart in order to be accommodated.

However, drug injection through the skin does not have to be achieved with the drug in a standard liquid form. Solid form drugs have been successfully administered with the PowderJect system, which uses a compressed gas source to accelerate powdered drugs to a velocity at which they can penetrate the outer layers of the skin. This system typically employs powdered drug particles of less than 100 microns in diameter, which require a velocity of several hundred meters per second in order to penetrate human tissue. However the system has its own inherent problems such as controlled delivery.

It has also been shown in the past that solid rods or splinters of a therapeutic compound can be pushed, at a relatively low velocity, into the skin without the requirement for a needle although more traditionally these are delivered as implants.

The current transdermal drug delivery techniques can thus be categorised into groups based on the drug form and the velocity of the injection as set out in table 1 below:

TABLE 1

| Drug Injection Velocity | Drug Form | |
|---|---|---|
| | Liquid | Solid |
| High Velocity | Liquid Jet Injector | PowderJect Systems Drug darts |
| Low Velocity | Needle and Syringe | Drug 'Splinters' |

Drug darts are disclosed in a number of publications. WO 96/40351 (American Cyanamid) discloses an implant dart with a head of a solid plastics material which takes the form of a blade and a tubular body that contains one or more sustained release drug delivery implant packages. Flexible stabilizing wings are provided on either side of the dart head which serve as a lock or barb to prevent the dart being pulled out after entry. The dart has on outside diameter of about 7 mm and a length of about 45 mm and is delivered with an injection gun which fires the dart into an animal, but not a human, when a trigger is released. The propulsion mechanism delivers a force sufficient to impart a high accelerating velocity of from 40-60 mph on the dart. To inject the dart at low speed it is necessary to make a small incision in the animal and operate the push bar manually.

U.S. Pat. Nos. 3,948,263 and 4,326,524 also disclose ballistic delivery devices. U.S. Pat. No. 3,948,263 discloses a ballistic implant which is fired from a 0.25 calibre rifle. The projectile exits at about 900 ft/sec and can travel 20-40 ft before implanting into muscle some 1-2 inches beneath the skin. U.S. Pat No. 4326 524 discloses a solid dose ballistic projectile formed entirely of a cohesive mixture comprising biologically active material, in the form of grindable solid particles and a binder which is capable of withstanding the stresses imparted on impact. The projectile has a body portion with a diameter of from 4.5 to 7.6 mm, with a conical nose portion with a base diameter smaller than the diameter of the body such that a slight shoulder region is formed between the body and the nose. The end remote from the nose is preferably concave to aid flight.

GB 2365100 is another example of a remote ballistic delivery device which is fired and attains velocities of greater than 500 m/s. In contrast to those described above the device is slowed on impact so that it does not enter the body but instead the device's nose is moved back such that a needle enters the body, and a drug is injected. Such a device is not needleless.

CA1019638 discloses a projectile which is launched by a conventional air gun or bow. It comprises a head piece and a shaft, the head piece pierces the animals flesh and the shaft breaks away. In one embodiment the head piece is made of a porous material which retains a liquid drug through capillary action through launch and impact and which releases it by diffusion when it is inserted into the animal. In a second embodiment the head piece takes the form of a hardened cake. To aid penetration a metal or plastics tip may be provided. The drug delivering element remaining in the skin is about 3 mm diameter by 13 mm in length.

U.S. Pat. No. 3,901,158 Ferb discloses a hypodermic projectile which is again fired from a rifle or pistol. It comprises a shatterable front end of plastic or glass which breaks on impact releasing the liquid contents.

None of the described high velocity devices bear any resemblance to the present invention in which the at least one therapeutic compound or a formulation comprising the at least one therapeutic compound is pushed at low velocity from a device which contacts the skin and in which the pioneer projectile is water soluble, lipid soluble or otherwise biodegradable in the human or animal and is furthermore significantly smaller having a width or diameter of less than 3 mm in width, more preferably still less than 2.5 mm through 2 mm and 1.5 mm to about 1 mm in width; a height of less than 10 mm in height, more preferably about 1.5 to 2 mm in height and an aspect ratio of less than 1:8, preferably less than 1:6, more preferably less than 1:4, more preferably still less than 1:3, and most preferably about 1:1.5.

High velocity liquid systems are exemplified by U.S. Pat. No. 116,313 Mc Gregor. Liquid is first ejected from a small orifice in a probe at a very high velocity and pressure which will penetrate the skin and then the main charge of liquid is ejected at a lower velocity into the channel formed by the initial penetration EP0139286 (Sumitomo Chemical Co Limited) discloses sustained-release preparations in the form of needle like or bar like shapes, which comprise an active ingredient and a pharmaceutically acceptable biodegradable carrier. The sustained-release preparation can be administered to the body by injection by pushing it through a hollow needle or by implantation.

WO 94/22423 (Bukh Meditec A/S) discloses a drug administration system. The method of parenteral administration comprises administering a drug substance by penetrating the skin or the mucosa of a human or an animal by a body with an appropriately formed solid pharmaceutical composition. The body of the pharmaceutical composition may be needle shaped so as to avoid external penetration equipment. The solid pharmaceutical composition comprises at least one drug substance and has a shape and/or strength to enable penetration.

The composition is made by mixing a material, preferably a polymer and optionally a filler with an active drug substance; extruding the mixture to form an elongate body; drying it and forming a pointed end.

U.S. Pat. Nos. 5,542,920, 6,117,443 and 6,120,786 (Cherif Cheikh) all disclose needle-less parenteral introduction devices. A medicament is made in the form of a solid needle having a pointed end that has sufficient structural integrity to penetrate the skin. The needles are less than 2 mm, preferably 0.2 to 0.8 mm, in diameter and 10 to 30 mm in length.

U.S. Pat. No. 6,102,896 (Roser) is primarily directed to a disposable injector device for injecting controlled release water soluble glass needles. It however also recognises that these glass needles, which are about 1 mm in diameter by 10 mm in length and contain a medicament may also be used as pioneer projectiles to produce a low resistance pathway through the tissue along which a liquid suspension (exemplified as a drug in a suspension of PFC fluid) can flow. This document appears the first and only document to recognise that a dissolvable pioneer projectile may be used to enable the introduction of a medicament. It however fails to recognise that it may be used as a general technique for introducing medicaments in other forms. Indeed this is readily apparent from the document in which a dry powdered formulation is made into a non viscous liquid by suspending it in PFC.

SUMMARY OF THE INVENTION

The present invention takes the concept of using a pioneer projection (as disclosed in U.S. Pat. No. 6,102,896) further and follows from the applicants recognition that a pioneer projectile can be used as a means for introducing medicaments in forms other than a free flowing, non viscous liquid.

According to a first aspect of the present invention there is provided a method of delivering at least one therapeutic compound or a formulation containing the at least one therapeutic compound to a human or animal in the form of a needleless injection comprising:

i) Penetrating the skin with a water soluble, lipid soluble or otherwise biodegradable pioneer projectile having a diameter of less than 3 mm which is left in the human or animal; and ii) Introducing directly, or substantially directly, behind the pioneer projectile, the at least one therapeutic compound or the formulation containing the at least one therapeutic compound, which at least one therapeutic compound or the formulation containing the at least one therapeutic compound is provided and delivered in a contained state.

By contained state is meant either:

i) As a liquid contained by a membrane;

ii) As a liquid with a viscosity of at least 5000 centipoises (the viscosity of honey), more particularly at least 50,000 (the consistency of mayonnaise) and most preferably still at least 100,000 (the consistency of peanut butter), such that the liquid has characteristics more akin to a solid than a liquid i.e. they have a definite shape as well as volume (and are not readily free flowing);

iii) As a semi-solid (having a viscosity and rigidity intermediate that of a solid or a liquid);

iv) As a paste (having a soft malleable consistency);

v) As a gel (a liquid dispersed in a solid) which materials can all be considered to have a degree of stiffness; or vi) As a solid (a state in which the matter retains its own shape).

Introducing a medicament in such a contained state has advantages in that splash back and seepage can be avoided and more controlled dosages delivered when compared to a following non viscous liquid formulation. The viscous, semi solid or solid nature of the medicament ensures that the pioneer projectile is pushed to the requisite depth and is followed by the medicament rather than seeping around the sides of the projectile. The semi solid formulations, gels, pastes and solids are also generally more stable than liquid formulations and are more patient compliable.

Furthermore it will be appreciated that by introducing the medicament in a form other than as a non viscous liquid behind a pioneer projectile it is possible to tailor the characteristics of the medicament for optimum pharmacokinetic delivery rather than for penetration.

Similarly the pioneer projectile can be developed to have optimised penetrating capabilities independent of the medicament.

Preferably the pioneer projectile is independent of the at least one therapeutic compound or the formulation containing the at least one therapeutic compound.

Alternatively the pioneer projectile is independent of yet forms an integral part of the at least one therapeutic compound or the formulation containing the at least one therapeutic compound.

Most preferably the pioneer projectile forms a head to the at least one therapeutic compound or the formulation containing the at least one therapeutic compound.

The at least one therapeutic compound or the formulation containing the at least one therapeutic compound can take a number of forms.

In one embodiment the at least one therapeutic compound or the formulation containing the at least one therapeutic compound is a liquid contained in a water soluble, lipid soluble or otherwise biodegradable membrane.

In another embodiment the at least one therapeutic compound or the formulation containing the at least one therapeutic compound is provided in a solid form such as, for example, crystals, particles, granules, beads, rods, discs or a combination thereof.

In yet another embodiment the at least one therapeutic compound or the formulation containing the at least one therapeutic compound is provided as a viscous liquid, semi solid, gel or paste which may be further supported, if desirable, by a water soluble lipid soluble or otherwise biodegradable membrane.

In the method of the invention the skin is penetrated and the therapeutic compound administered at a low velocity. By low velocity is meant less than 100 m/s. Preferably the velocity is less than 10 m/s, more preferably still less than 5 m/s and most preferably in the order of a few m/s.

Since the injectate is pushed at a low velocity rather than fired at a high velocity it is possible to ensure that the dosage is always delivered to the correct (and same) depth under the skin. This means that the system can be used on different skin types and skin locations and the dosage will still be delivered to the same depth.

According to a second aspect of the invention there is provided a method of facilitating the delivery of at least one therapeutic compound or a formulation containing the at least one therapeutic compound to a human or animal as a needleless injection comprising:
  i) Providing a water soluble, lipid soluble or otherwise biodegradable pioneer projectile having a diameter of less than 3 mm capable of penetrating the human or animals skin; and
  ii) Providing directly, or substantially directly, behind the pioneer projectile, the at least one therapeutic compound or the formulation containing the at least one therapeutic compound in a contained state.

The act of pushing the at least one therapeutic compound in the contained state causes the pioneer projectile to penetrate the human or animals skin and the therapeutic compound or the formulation containing the at least one therapeutic compound follows the pioneer projectile and is introduced into the human or animal in the contained state.

The invention also extends to novel pioneer projectiles.

According to a third aspect of the present invention there is provided a water soluble, lipid soluble or otherwise biodegradable pioneer projectile having a diameter of less than 3 mm, and which is capable of penetrating the skin of a human or animal to thereby facilitate the injection of at least one following therapeutic compound or therapeutic compound containing formulation in a contained state, comprising:
  i) A first "penetrating" face which in use penetrates the human or animals skin and
  ii) Remote from the first face a second "driven" face which in the course of injection is the face upon which a driving force is exerted through the contained therapeutic compound or therapeutic compound containing formulation; characterised in that said pioneer projectile has an aspect ratio (width to height) of less than 1:10.

Because the pioneer projectile has been developed separately of the medication it has been possible to reduce its size from one of at least 10 mm in length to about a few millimeters. It has also been possible to optimise its shape such that it functions as a leading head or tip for a following contained formulation the two components forming an injectate.

Preferably the pioneer projectile has an aspect ratio of less than 1:8, preferably less than 1:6, more preferably less than 1:4, more preferably still less than 1:3, and most preferably about 1:1.5.

Preferably the pioneer projectile is less than 3 mm in width, more preferably still less than 2.5 mm through 2 mm and 1.5 mm to about 1 mm in width.

Preferably the pioneer is less than 10 mm in height, more preferably about 1.5 to 2 mm in height. By reducing the height to a minimum it is possible to maximise the amount of therapeutic compound being injected. In this regard it should be noted that if the combined pioneer projectile and following drug formulation is too long it might not be possible to deliver the drug to the optimum depth.

In one embodiment the pioneer projectile is free of any therapeutic compound. In another embodiment it comprises at least one therapeutic compound. Thus, for example it might be beneficial to include, for example, an antibiotic in the pioneer projectile or have it release a therapeutic compound at a different rate to the formulation in, for example, the case of insulin injections.

The skin penetrating face of the pioneer projectile preferably comprises a cutting element to facilitate entry. This may take the form of a sharp point or an oblique edge. Alternatively the skin penetrating face may be blunt or gently curved.

In one embodiment the face for contacting the therapeutic compound or therapeutic compound containing formulation in a contained state is flat. Alternatively it may be concave or otherwise hollowed to facilitate pushing and formulation containment.

The pioneer projectile may be made of any suitable material. Suitable materials are those hard and rigid enough to facilitate penetration at low velocities. Preferred materials include glassy materials e.g. the sugar glasses as noted in WO 98/41188 which materials are included herein by reference. The term "sugar" thus covers not only disaccharide sugars, such as, trehalose, but also monosaccharide sugars and their non reducing derivatives, such as, sugar alcohols including: mannitol, inositol, xylitol, ribitol and the like, which form a general class of stabilising glass-forming sugars and sugar derivatives. The term "sugar glass" is to be understood as covering not only glasses which are readily and rapidly dissolved in an aqueous environment, such as, trehalose but also sugar glasses in which the sugar molecule has been modified by the attachment of one or more hydrophobic side chains to make the glass more slowly soluble in bodily fluids than the native sugar in order to give controlled release characteristics.

In some circumstances the pioneer projectile may comprise a barrier material over at least the face that contacts the therapeutic compound in a contained state or vice versa such that the respective components will not react with one another.

The invention also extends to novel formulations.

According to a fourth aspect of the present invention there is provided a therapeutic compound or therapeutic compound containing formulation which is held in a contained state and adapted for introduction into a human or animal in the form of a needleless injection behind a water soluble, lipid soluble or otherwise biodegradable pioneer projectile having a diameter of less than 3 mm.

Preferably the formulation comprises less than 50 mg of therapeutic compound in a volume of less than 50 mm$^3$, more preferably less than 10 mg of therapeutic compound in a volume of less than 10 mm$^3$.

The therapeutic compound or therapeutic compound containing formulation may be provided as a liquid contained in water soluble, lipid soluble or otherwise biodegradable membrane.

In an alternative embodiment the therapeutic compound or therapeutic compound containing formulation is provided in a solid form comprising for example crystals, particles, granules, beads, rods, discs or a combination thereof which are generally likely to be more stable than traditional non-viscous liquid formulations with a viscosity similar to that of water e.g.1 Centipoise or glucose e.g. 500 Centipoises.

In a preferred embodiment the therapeutic compound or therapeutic compound containing formulation is provided as a semi solid, gel or paste. In this form it is particularly patient compliant and the therapeutic compound is generally likely to be more stable than if it were in a traditional non-viscous liquid formulation.

Where the therapeutic compound or therapeutic compound containing formulation is a viscous liquid, it preferably has a viscosity of at least 10,000 Centipoises more preferably at least 50,000 Centipoises and more preferably still at least 100,000 Centipoises.

The formulation may comprise an end piece beyond the therapeutic compound or therapeutic compound which is free of the "active" being injected thus ensuring that the entire therapeutic compound enters the patient in a unit dose rather than risk under or over dosing.

The therapeutic compound or therapeutic compound containing formulation may comprise a plurality of differently formulated elements.

The therapeutic compound or therapeutic compound containing formulation may be packaged in a cap, cartridge, carousel or cassette.

The invention also extends to an injectate comprising a pioneer projectile and a therapeutic compound or therapeutic compound containing formulation.

According to a fifth aspect of the present invention there is provided a needleless injectate for injection comprising:
a) A water soluble, lipid soluble or otherwise biodegradable pioneer projectile having a diameter of less than 3 mm; and
b) A therapeutic compound or therapeutic compound containing formulation which is held in a contained state behind the pioneer projectile.

These components are as previously described.

The pioneer projectile and therapeutic compound or therapeutic compound containing formulation may both be water soluble, lipid soluble or otherwise biodegradable to differing degrees.

A barrier may be provided between the pioneer projectile and the therapeutic compound or therapeutic compound containing formulation.

The injectate may be contained/packaged in a cap, cartridge, carousel or cassette optionally together with a means, e.g. an ejector pin, for pushing the pioneer injectate out of its container.

Alternatively the pioneer projectile and the therapeutic compound or therapeutic compound containing formulation are contained/packaged in separate caps, cartridges, carousels or cassettes.

The invention also extends to a device for injecting a pioneer projectile and a therapeutic compound or therapeutic compound containing formulation.

According to a sixth aspect of the present invention there is provided a needleless device (60) for injecting a water soluble, lipid soluble or otherwise biodegradable pioneer projectile (10) having a diameter of less than 3 mm and at least one contained therapeutic compound or therapeutic compound containing formulation (42) into a human or animal body, said device comprises a housing (62) containing a mechanism (92) capable of generating a force which will cause a striker (84) to travel along a striker guide (86), said housing having an end face (100) which is in operative communication with a component (72) comprising a casing (74) having an aperture (76) in which is mounted an ejector pin (78) and, therebelow, an injectate (40) comprising a pioneer projectile (10) and a formulation (42) such that in use the striker will contact the ejector pin and the injectate will be pushed out of the casing as a single unit into the human or animal body.

The reference numerals given above are non-limiting but have been included solely for the purpose of assisting the reader.

The term ejector pin is intented to cover a pin, piston, rod or like member which functions to push the injectate from the aperture.

The power source for initiating or assisting the pushing may be a mechanical spring in the form of, for example, a coiled spring or a lever spring. Alternatively, a gas spring might be used or even an electrically powered system. A mechanical spring would allow reuse of the delivery system although this would mean the user has to recharge the spring between administrations. Alternatively, the spring (mechanical or gas) could be precharged during manufacture so that it can only be used once and then the whole system would be thrown away. In a reusable device there will be a throw away component containing the pioneer projectile or the pioneer projectile and the therapeutic compound or therapeutic compound containing formulation.

The device preferably incorporates a safety mechanism to avoid accidental actuation. Actuation might be triggered with a push button on the device but preferably would be undertaken by pushing the device against the skin thus ensuring good contact with the skin on actuation.

In a reusable device the reusable component and the throw away component comprise means by which they are connected to one another.

The device may be adapted to inject multiple doses either sequentially or simultaneously. In one embodiment the device comprises a cartridge, carousels or cassette containing a plurality of pioneer projectiles or a plurality of injectates comprising a pioneer projectile and a therapeutic compound or therapeutic compound containing formulation.

In another embodiment the device comprises a cap containing a single pioneer projectile and a single unit dose of the therapeutic compound or therapeutic compound containing formulation.

The various aspects described above give rise to a system having a number of advantages over the prior art delivery methods and some of these are noted in table 2 below:

TABLE 2

| | Benefit | Justification |
|---|---|---|
| 1 | Can use formulations with Increased Product | Many drugs are more stable in solid form than in a liquid state. A viscous liquid formulation would be more akin to a solid drug in terms of its stability |

TABLE 2-continued

| Benefit | Justification |
| --- | --- |
| Stability. | characteristics because of the excipients that can be used |
| 2 Improved Product Storage | The increased stability with some compounds may allow storage of the final delivery system at room temperature rather than requiring refrigeration |
| 3 Reduced Risk Of Cross Infection | Without the need for needles there is a reduced risk of blood borne diseases |
| 4 Small Device Size | Spring, trigger, injectate and piston are the main components required |
| 5 Cheap Device | A spring is a cheap power source. Small overall number of device components |
| 6 Reusable Device | The design can allow for the spring to be primed for reuse. Disposable components would be small in terms of size and cost but would include the component holding the injectate or pioneer projectile |
| 7 Variable Power System | A spring-powered device could allow the tension on the spring to be altered for different skin types and skin positions on the body, if necessary. |
| 8 Small Skin Response | As experienced with splinters |
| 9 Quiet Device | Actuation of a spring powered delivery system will be quiet |
| 10 Easy to Understand Delivery System | Easy to comprehend the forces involved in pushing a foreign body into the skin to a known depth. Easy to measure the physical characteristics required for a 'dose' of injectate of this size |
| 11 Variable Dose | With a viscous injectate it will be possible to alter the dose injected |
| 12 Self Injection | With a simple system patients can inject themselves, thus reducing healthcare costs |
| 13 Controlled Depth Of Penetration Of The Delivered Dose | Pushing the injectate into the skin rather than firing it enables a consistent and controlled depth of penetration in the skin |
| 14 Large Doses Achievable | Large doses of one or more drugs are achievable by having one or more doses of injectate administered in the same injection |

The concept behind the invention allows for a simple needleless drug delivery device that pushes a drug in a "contained" state.

A semi solid, paste or gel is the preferred form since unlike a non-viscous liquid it would follow the pioneer projectile. (A non-viscous liquid can "splash back" and more easily seep around the track formed by the pioneer projectile.) Its stiffness relative to a non-viscous liquid also means it is easier to push than a non-viscous liquid material. The more solid in nature the better this is. However from a comfort perspective a semi solid or paste or gel is more likely to be patient compliant and dissolve more readily in the body.

The delivery device for delivering such an injectate (pioneer projectile and formulation) could take a number of forms and one such device is described by way of example.

The device described is a spring-powered device with the spring, triggering the pushing of a pin. The pin then engages the injectate to push it into the skin with the pin being stopped by either an end stop within the device or by coming into contact with the skin, preferably over a relatively wide area (compared to the injectate) to reduce the force felt on the skin.

If the device is to be reusable then the component holding the injectate might be detached from the rest of the device and thrown away and a new disposable component attached before the next injection. The injection itself would occur in a matter of milliseconds after actuation and would seem instantaneous as far as the user is concerned. Alternatively the formulation might be injected from, for example, a tube and a new pioneer projectile would be required for a further injection.

The various aspects of the invention will now be described, by way of example only, with reference to the following drawings and Examples.

BRIEF DESCRIPTION OF THE DRAWINGS

FIGS. 5a-c are a plan view, side elevation and end elevation respectively of a pioneer projectile with an oblique cutting edge;

FIGS. 6a-c are a plan view, side elevation and end elevation respectively of a pioneer projectile with a central piercing point and faceted sides;

FIGS. 7a-c are a plan view, side elevation and end elevation respectively of a pioneer projectile with a central cutting edge;

FIGS. 8a-c are a plan view, side elevation and end elevation respectively of a pioneer projectile with a central piercing point;

DETAILED DESCRIPTION

Figure 1A:
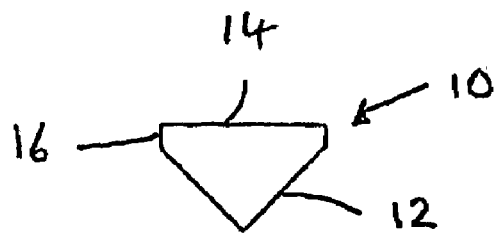
FIG. 1a-e are embodiments of pioneer projectiles of varying shapes and sizes.

Referring to the drawings, FIG. 1a is a side elevation of a pioneer projectile 10 according to one aspect of the present invention. It is made of a crystalline or amorphous material, preferably a glassy material, (e.g. a sugar glass such as trehalose, palatinit, glucopyranosyl sorbitol, glucopyranosyl mannitol, lactitol or monosaccharide alcohols such as mannitol or inositol) which is water-soluble and dissolves in the body. The material may include a hardening agent, such as, for example, povidone (pvp). The pioneer projectile comprises a penetrating face 12 comprising one of more facets, which has a central point, one or more guiding faces 16 for guiding the pioneer projectile within a central aperture or chamber of a needleless device for injecting an injectate (comprising the pioneer projectile and a formulation) thus ensuring the pioneer projectile meets the skin at a suitable angle to aid penetration, and a driven face 14. The pioneer projectile has an aspect ratio (width W to height H) of about 1.25:1.

The pioneer projectile can however take a number of forms and some further embodiments are illustrated in FIGS. 1b-d, FIGS. 2a-2c, FIGS. 3a-d, FIGS. 4a-c, FIGS. 5a-c, FIGS. 6a-c; FIGS. 7a-c and FIGS. 8a-c.

Figure 1B:
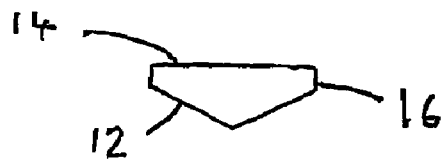
Figure 1C:
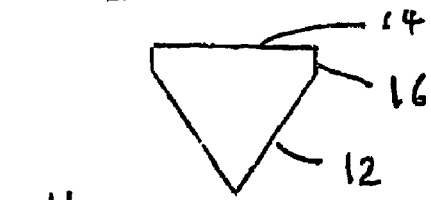
Figure 1D:
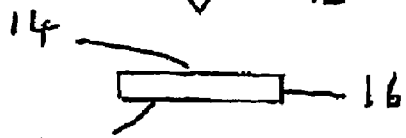
Figure 1E:
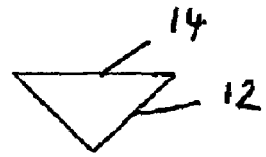

Briefly: FIG. 1b illustrates a pioneer projectile with a very small aspect ratio of about 1:0.5; FIG. 1c illustrates a pioneer projectile with an aspect ratio of about 1:2; FIG. 1d illustrates a pioneer projectile with a blunt and planar penetrating face 12, and an aspect ratio of about 1:0.2; and FIG. 1e illustrates a pioneer projectile which does not have a guiding face 16 but consists of a penetrating face 12 and a driven face 14.

Figure 2A:
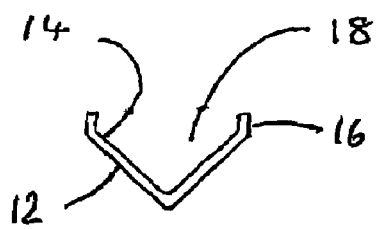
FIGS. 2a-c are embodiments of pioneer projectiles with hollow driven faces.
Figure 2B:
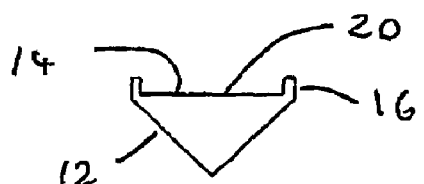
Figure 2C:
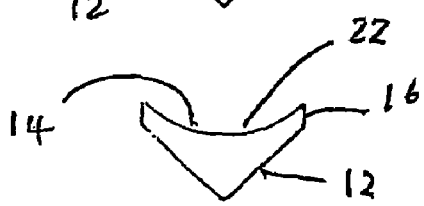
Figure 3A:
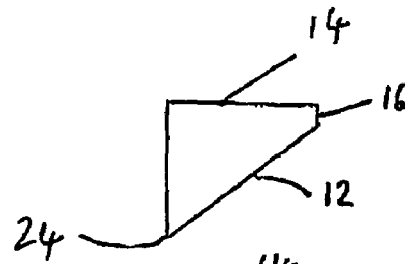
FIGS. 3a-d are embodiments of pioneer projectiles with an oblique cutting edge.
Figure 3B:
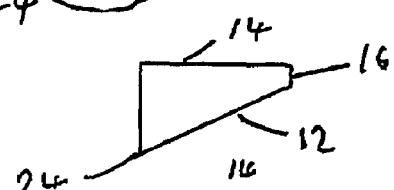
Figure 3C:
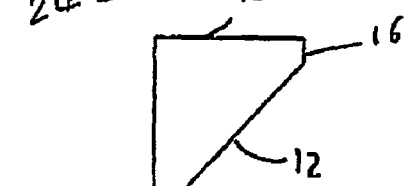
Figure 3D:
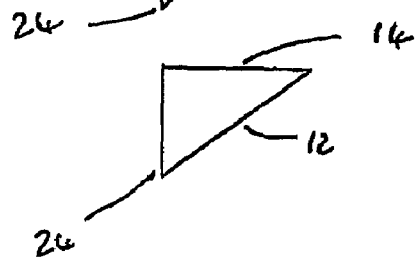
Figure 4A:
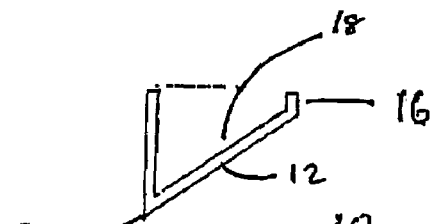
FIGS. 4a-c are embodiments of pioneer projectiles with an oblique cutting edge and hollow driven faces.
Figure 4B:
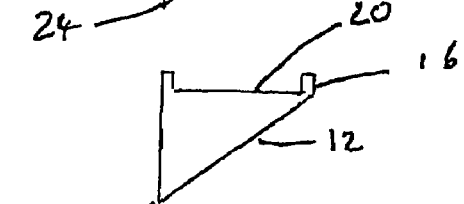
Figure 4C:
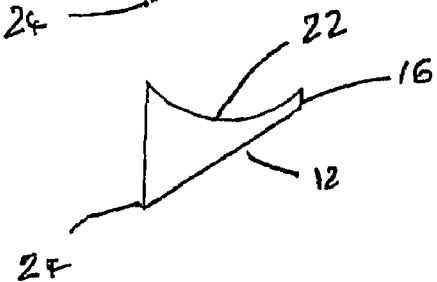

FIGS. 2a to 2c illustrate variations in the driven face 14. Thus in FIG. 2a the driven face is completely hollowed forming a void 18 which can hold, at least in part, at least one therapeutic compound or compound containing formulation. In FIG. 2b the hollow 18 has a flat bottom 20 and in FIG. 2c it has a concave bottom 22.

Of course, the penetrating face 12 need not have a central point and FIGS. 3a-d, and 4a-c illustrate embodiments in which the pioneer projectiles have an oblique cutting edge 24.

Figure 5A:
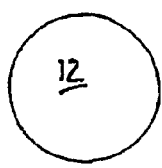

The shape of the penetrating face can, as noted above, take a number of forms as exemplified with reference to FIGS. 5-8. In each of these FIGS. a) is a plan view; b) is a side elevation and c) is an end elevation. Thus:

In FIG. 5 the pioneer projectile is circular in x-section (FIG. 5a), has an oblique cutting edge 24 (FIG. 5b), and a planar penetrating face 12 (FIG. 5c).

Figure 6A:
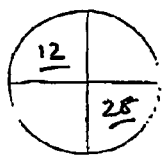

In FIG. 6 the pioneer projectile is circular in x-section (FIG. 6a), has a central point 26 (FIG. 6b), and four facets 28 making up the penetrating face 12 (FIG. 6c).

Figure 7A:
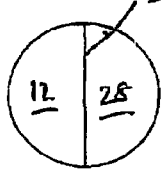

In FIG. 7 the pioneer projectile is circular in x-section (FIG. 7a), has a central cutting edge 30 (FIG. 7b), and two facets 28 making up the penetrating face 12 (FIG. 7c).

Figure 8A:
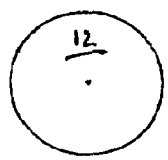

In FIG. 8 the pioneer projectile is circular in x-section (FIG. 8a), has a conical penetrating face (FIG. 8b), culminating in a point 30 and a penetrating face 12 (FIG. 8c).

Of course the pioneer projectile need not be circular in cross section but could be, for example, three sided (triangular), four sided (square) or indeed any other suitable shape.

A pioneer projectile might be manufactured in a number of ways such as by moulding, extrusion or sectioning a rod of the material.

Preferably the pioneer projectile will dissolve in the tissue in a matter of minutes or hours depending on the material used.

The pioneer projectile together with at least one therapeutic compound or formulation forms an injectate.

The physical characteristics of the formulation are very important to ensure that the injectate can be administered to the skin in a reliable and repeatable manner The formulation could take a number of forms:

In one embodiment it might take the form of a paste. This can be achieved by mixing the active drug with the appropriate excipients to end up with consistency, say, like toothpaste. The excipients would obviously need to maintain the active ingredient in a condition such that it was still active during manufacture, storage and administration.

In other embodiments the formulation will be a semi solid, gel, solid or contained liquid.

The therapeutic component of the formulation might be present in one or more of the following formats:

1. Pure drug;
2. With excipients to alter the physical characteristic of the material;
3. With excipients to bulk out the active ingredient;
4. With excipients to buffer the active ingredient;
5. With excipients to change the release profile of the active ingredient; and
6. As a mixture of more than one therapeutic compound.

The formulation can be designed to give the desired release profile for the application. This might involve either a sustained release formulation or a quick dissolving formulation for immediate release into the body. In some cases, such as for the administration of insulin, a formulation might be required that provides an immediate release of some of the therapeutic compound and then a sustained release of another component in the formulation. This might for example be achieved by having the formulation in a plurality of parts or by incorporating a medicament into the pioneer projectile.

Alternatively the therapeutic compound might be formulated as small beads. A number of the beads could be lined up in the device behind a pioneer projectile. On actuation of the device the pioneer projectile pierces the skin and the beads are pushed into the skin behind the pioneer projectile.

The therapeutic component of the formulation must of course not react with the material used for the pioneer projectile or the materials used in the delivery system.

FIGS. 9 to 15 are some embodiments illustrating injectates and formulations of the invention.

Figure 9:
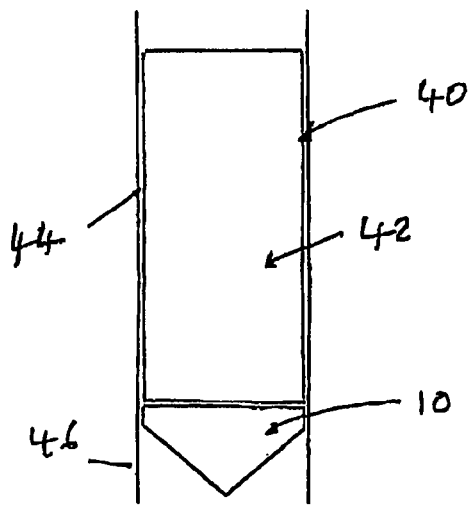
FIG. 9 is one embodiment of an injectate of the invention shown housed in a support or device chamber.

In FIG. 9 an injectate 40 comprises a pioneer projectile 10 and a formulation 42. The formulation is in a contained state supported by its own viscosity or a membrane 44. The formulation is thus a contained liquid or a solid. The injectate may be self-supporting or contained in an optional support 46 which may be a chamber 76 of a device or a throwaway component.

Figure 10:
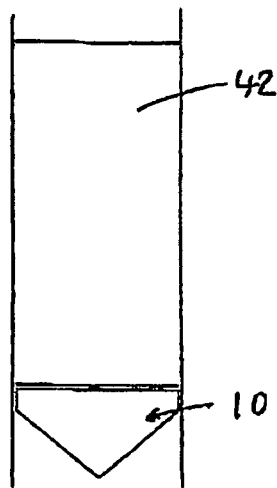
FIG. 10 is another embodiment of an injectate of the invention shown housed in a support or device chamber.

In FIG. 10 the formulation is a high viscosity liquid, gel, paste or semi-solid.

Figure 11:
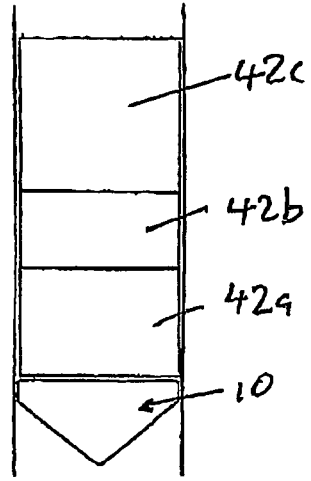
FIG. 11 is another embodiment of an injectate of the invention shown housed in a support or device chamber.

FIG. 11 illustrates an injectate comprising a plurality of different formulations 42a, 42b and 42c. These could be formulations with different release profiles or different active ingredients, for example combination therapies. Though not illustrated there could be membranes between the components e.g. lipid soluble membranes between water-soluble formulations and or an end piece.

Figure 12:
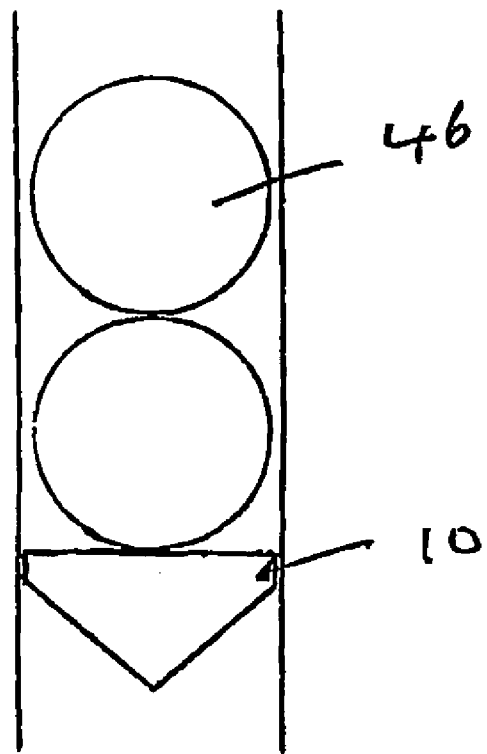
FIG. 12 is another embodiment of an injectate of the invention shown housed in a support or device chamber.
Figure 13:
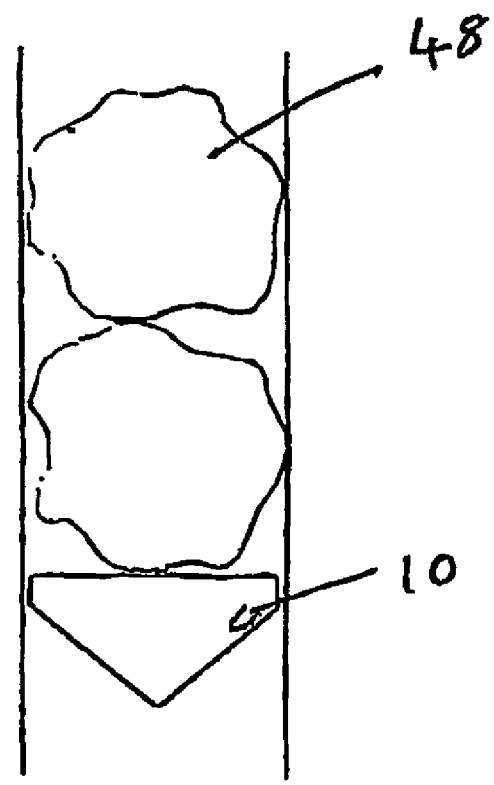
FIG. 13 is another embodiment of an injectate of the invention shown housed in a support or device chamber.
Figure 14:
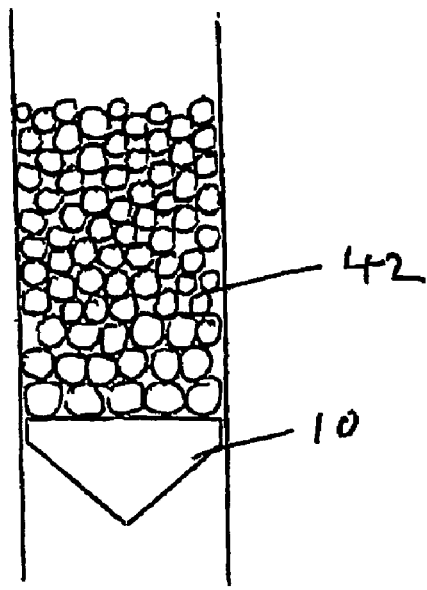
FIG. 14 is another embodiment of an injectate of the invention shown housed in a support or device chamber.

FIGS. 12, 13 and 14 illustrate injectates with different solid formulations. In FIG. 12 the solid formulation takes the form of beads 46. In FIG. 13 and 14 they are granules, particles or crystals 48.

Figure 15:
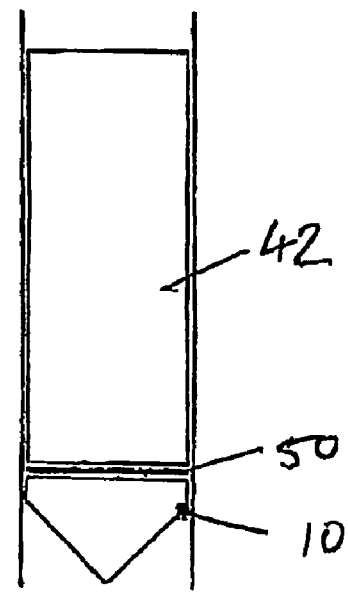
FIG. 15 is another embodiment of an injectate of the invention shown housed in a support or device chamber.

In FIG. 15 a barrier 50 is shown between the formulation 42 and the pioneer projectile 10.

The skilled man will of course realise that the features illustrated with reference to one embodiment could easily be applied to other embodiments.

An injectate will be introduced into a human or animal using a device that injects the injectate in a needleless manner.

Figure 16:
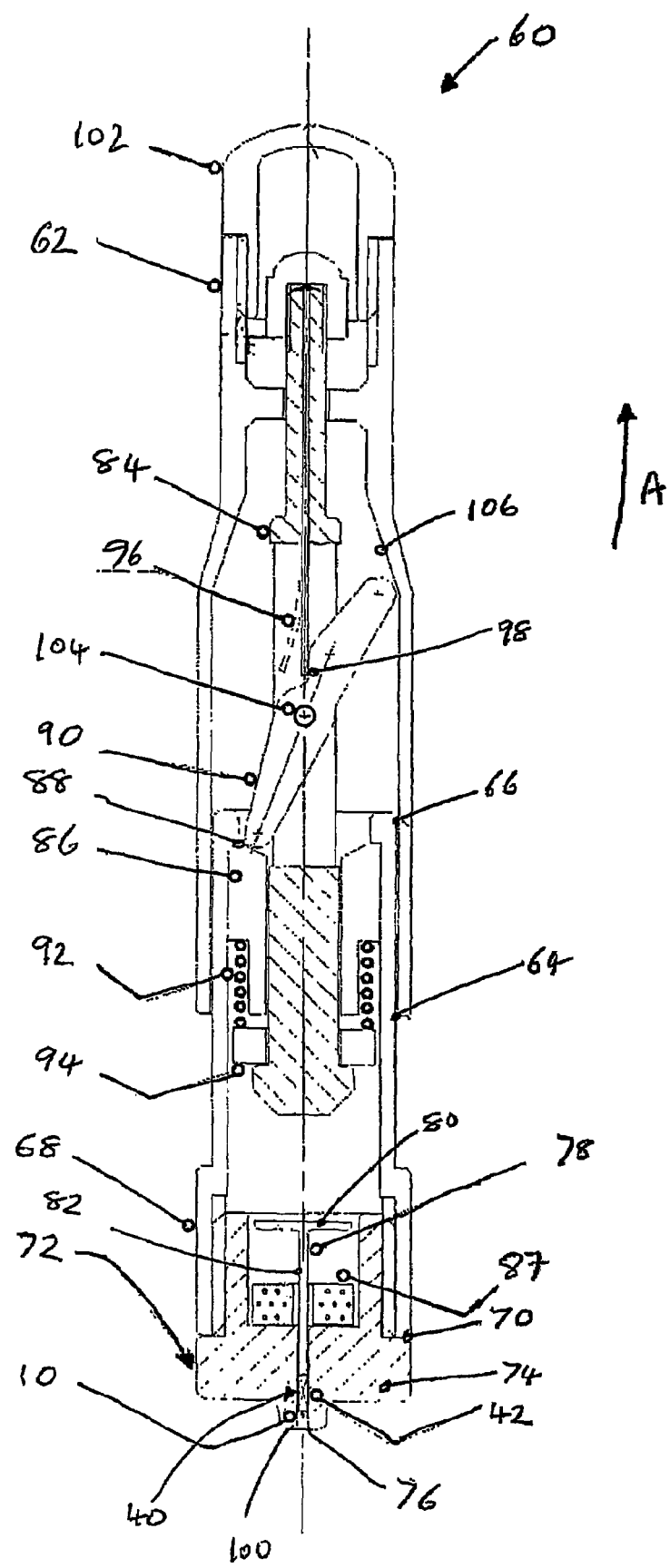
FIG. 16 is cross sectional view of a delivery device of the invention.

One such device is illustrated by way of example only in FIG. 16.

The needleless injection device 60 is shown in the primed position. It comprises an outer housing or holder 62 the lowermost end 64 of which is slidably mounted over the uppermost end 66 of an innermost casing 68.

At the lowermost end 70 of innermost casing 68 is fitted a disposable component 72 such as, for example, a drug cassette. The disposable component comprises a casing 74 having a central aperture or chamber 76 in which is mounted the injectate 40 comprising the pioneer projectile 10 and the formulate 42. A large headed ejector pin 78 comprising a flat head 80 and an elongate body 82 is positioned over the injectate 40 so that when the ejector pin is contacted, in use, by a striker 84 it is pushed along the aperture or chamber 76 and out into the patient. A resilient member 87, such as a rubber block urges the ejector pin back a little after injection.

The disposable component 72 is loaded into the needleless injection device, by for example, screwing it into the lowermost end 70 of the inner housing 68. Mounted within the innermost housing 68 is a striker guide 86 having a surface 88 which maintains a detent 90 in the loaded position (shown) and houses an actuating mechanism or spring 92 and spring follower 94.

The disposable component 72 is shaped such that when it is in contact with the skin it pre-tensions it prior to actuation. This ensures that the dosage will penetrate the skin rather than just stretch the skin.

The injector pin 78 is designed to push the injectate beyond the end of the device by up to (say) 2.5 mm. This means that the end of the injector pin (which preferably has the same profile and diameter as the end of the pioneer projectile) might just penetrate the skin but it would ensure that the injectate has been fully administered into the skin.

Prior to actuation, the tip of the injectate might be in contact with the skin. However, it is preferred that the tip is a few millimeters away from the skin prior to actuation. This ensures that the injectate is moving when it impacts the skin and also ensures that the tip of the injectate does not start to dissolve, and therefore soften the tip, with any moisture from the skin surface when the device is placed on the skin.

To use the device 60 the outer most casing is retracted (pulled in the direction of arrow A) so that it slides against the innermost housing 68. This action causes the spring 92 to be compressed, and the detent to be moved from a vertical position to the position shown where it is held stable against surface 88. In the process a quill spring 96 stabilises the detent by abutting against a surface 98. Once loaded the disposable component, is screwed into the end 70 of the innermost housing 68 of the device 60.

The injector pin 78 that pushes the injectate into the skin is preferably, (but not necessarily) in contact with the injectate prior to actuation.

To actuate the device a user, for example, grips the device around the outer housing 62 with their thumb over the end cap 102. The end face 100 of the disposable component 72 is positioned against a patient's skin, which should be held taught, and the outer housing 62 is pushed in a direction away from arrow A. This action causes the outermost casing to slide over the inner housing 68. As it does so the detent is caused to rotate about it's axle 104 as a result of the detent riding up inclined wall 106. This forces the quill spring 96 out (as shown by the broken line). When the detent reaches a vertical position the coil spring releases its stored energy and assists in ensuring the striker 84 travels along the striker guide 86 until it contacts the head 80 of the ejector pin 78 with a force that causes the injectate 40 to pierce the skin. The ejector pin 78 continues to push the formulation 42 into the patient to the required depth, which is determined by the length of the injectate and the extent to which it is pushed by the ejector pin 78. The rubber stop 87 is squashed by the ejector pin head 80 during delivery of the injectate but the elastic properties of the rubber stop 87 enable the tip of the ejector pin to be withdrawn into the disposable component 72 of the device.

Injection Sites

The injectate could potentially be injected in a wide number of sites across the human or animal body. The easiest direction to administer the injectate is perpendicular to the skin and so with most skin sites this would mean penetrating the epidermis into the dermis and, depending on the skin thickness, into the subcutaneous layers or muscle. The 'best' injection sites might therefore be those where there is the smallest density of nerve endings to avoid any pain that might be associated with the injection. This might include injections to the back or to the lobe of the ear.

Alternatively, injection sites might include those with a thicker epidermis so that the injectate does not penetrate into the dermis where the nerve endings are located. The injectate might be injected obliquely into the skin so that it is located totally in the epidermis. The same result might be achieved by injection into a fold of skin that has been pinched.

The elastic properties of the skin can be employed to seal the skin after the injectate has been administered, as is often the case with splinters. This ensures the drug does not leak from the skin as it dissolves.

The most likely area of the body for drug administration with this technology is the stomach because of the high fat content and easy accessibility for self-administration. An alternative might be the thigh although this is often less accessible if the recipient is wearing trousers.

Product Applications

There are many possible product applications for this technology because of the doses that are achievable including therapeutic, prophylactic and diagnostic applications. Illustrative examples include, but are not limited to:

Conventional Vaccines—first and third world applications or veterinary applications;

Insulin;

Migraine Treatments; and

Hormones.

The term "at least one therapeutic compound or a formulation containing at least one therapeutic compound" as used in this application is intended to cover prophylactic and diagnostic applications as well as therapeutic applications.

The maximum dose that could be delivered using the technique will depend upon a number of factors. However, an injectate with an overall length of approximately 4.0 mm and a diameter of approximately 1.0 mm (similar to a 19 G venflon) would be sufficient to allow a dose of approximately 2 mg of a standard therapeutic in one administration. This magnitude of dose would be suitable for each of the applications exemplified above. If several doses of injectate are delivered simultaneously then there is the potential for an even larger number of applications.

Delivery of the injectate will be very quick and any pain associated with the delivery technique should not be any worse than a needle of similar dimensions. If the delivery technique were painful then it would be possible to anaesthetise the tissue prior to the injection. To avoid needles then this anaesthetic might be given with a patch, a spray or a cream.

EXAMPLE 1

Drug Splinters.

A rod of 0.9 mm diameter pencil lead was broken to lengths of approximately 6 mm and a point was sanded on one end of each length and a flat on the other to create solid splinters. The splinters were placed in a drug package and successfully administered to pig skin using a prototype delivery system.

EXAMPLE 2

Pioneer Projectile Followed by a Solid Rod.

The same pencil lead detailed in example 1 above was cut into short lengths of approximately 3 mm in length. These had a point sanded on one end and a flat on the other end to create pioneer projectiles. Further rods of the same pencil lead were cut at approximately 4 mm in length and had both ends sanded flat. When a pioneer projectile and a solid rod were placed in a drug package they were successfully administered to pig skin using a prototype delivery system.

EXAMPLE 3

Pioneer Projectile Followed by a Soft Rod.

A soft rod of wax was extruded through a die and rods of approximately 4 mm in length were cut with a flat at each end. Further sections were cut with a point at one end and a flat at the other end. When a pointed section (identical in shape and size to the splinter used in example 1) was administered to pig skin using a drug package the wax did not pierce the skin but was flattened on the skin surface. When a rod of the same waxy material was placed behind a pioneer projectile used in example 2 and administered to pig skin using a drug package then both the pioneer projectile and the waxy material were successfully delivered into the tissue. The wax material used for this experiment could easily be squashed between a finger and a thumb.

EXAMPLE 4

Pioneer Projectile Followed by Solid Beads.

Beads of diameters 0.5-0.75 mm were placed in a drug package behind a pioneer projectile as detailed in example 2. The pioneer projectile and all the beads were successfully administered to pig skin using a prototype delivery system.

The experiments outlined above demonstrated that a range of different materials could be delivered behind a solid pioneer projectile. Ideally it is preferred that the pioneer projectile is manufactured from pharmaceutical grade compounds that will dissolve in the target tissue. Two processes have been used to produce such pioneer projectiles as outlined below:

EXAMPLE 5

A hot melt of sugars is produced which can then be moulded into the correct form for a pioneer projectile or extruded to produce long rod. If an extrusion process is used then the pioneer projectiles can be cut to shape from the soft extrudate or the sharp ends of the pioneer projectile can be formed when the extrudate has solidified. This process produces a material similar to a boiled sweet which can be very hard and incorporate a sharp point on one end.

EXAMPLE 6

A mix of powders is produced using pharmaceutical grade sugars together with a hardening agent such as polyvinylpyrolidone (PVP). The powder blend is extruded through a die to produce a long rod of the compound. Some blends require a lubricant to facilitate the extrusion and binding process such as water or ethanol. The pioneer projectiles are formed by cutting the long rod into short sections. This process can be facilitated by using a hot knife. If necessary, the point or flat end of the pioneer projectile can be created by sanding or filing a short rod of the extrudate.

The invention claimed is:

1. A method of delivering at least one therapeutic compound to a human or animal in the form of a needleless injection comprising:
    providing an injection device comprising a casing having an aperture and a spring for storing energy, an ejector pin for pushing an injectate through the aperture wherein the injectate comprises at least one therapeutic compound;
    placing the aperture of the device close to or in contact with the skin of a human or animal;
    actuating the device by causing the spring to release its stored energy generating a force that causes the injector pin to engage the injectate and push it out of the aperture as a single unit;
    penetrating the skin of the human or animal with the injectate at a velocity of less than 100 m/s wherein the injectate has a maximum diameter of less than 3 mm and is left in the human or animal and wherein the ejector pin continues to push the injectate beyond the device and into the human or animal.

2. The method of claim 1 wherein the at least one therapeutic compound is selected from the group of prophylactic, diagnostic and therapeutic substances.

3. The method of claim 1 wherein the injectate further comprises a pioneer projectile.

4. The method of claim 1 wherein the spring is a mechanical spring.

5. The method of claim 1 wherein the therapeutic compound is intermixed with an excipient or excipients.

* * * * *